US00PP25838P3

(12) United States Plant Patent
Dobres

(10) Patent No.: US PP25,838 P3
(45) Date of Patent: Aug. 25, 2015

(54) ***ACHILLEA* PLANT NAMED 'NOVAACHDUS'**

(50) Latin Name: *Achillea hybrida*
Varietal Denomination: cv. Novaachdus

(71) Applicant: NovaFlora LLC, West Grove, PA (US)

(72) Inventor: Michael S. Dobres, Philadephia, PA (US)

(73) Assignee: CP Delaware, Inc., Wilmington, DE (US)

( * ) Notice: Subject to any disclaimer, the term of this patent is extended or adjusted under 35 U.S.C. 154(b) by 149 days.

(21) Appl. No.: 13/987,964

(22) Filed: Sep. 19, 2013

(65) Prior Publication Data

US 2015/0082500 P1 Mar. 19, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — Buchanan, Ingersoll & Rooney PC

(57) ABSTRACT

A new and distinct *Achillea* plant is provided that originated as a chance seedling from the open pollination of the 'Moonshine' variety (non-patented in the United States). Attractive fine silvery-green mature foliage is formed. The plant is early-flowering with the formation of soft light-yellow inflorescences that contrast nicely with the foliage coloration. The plant can be readily distinguished from the bright yellow inflorescences of the 'Moonshine' variety as well as other *Achillea* plants. A considerably more compact and shorter growth habit than the 'Moonshine' variety also is displayed. The plant is well suited for providing ornamentation in parks and gardens.

2 Drawing Sheets

Figure 1:
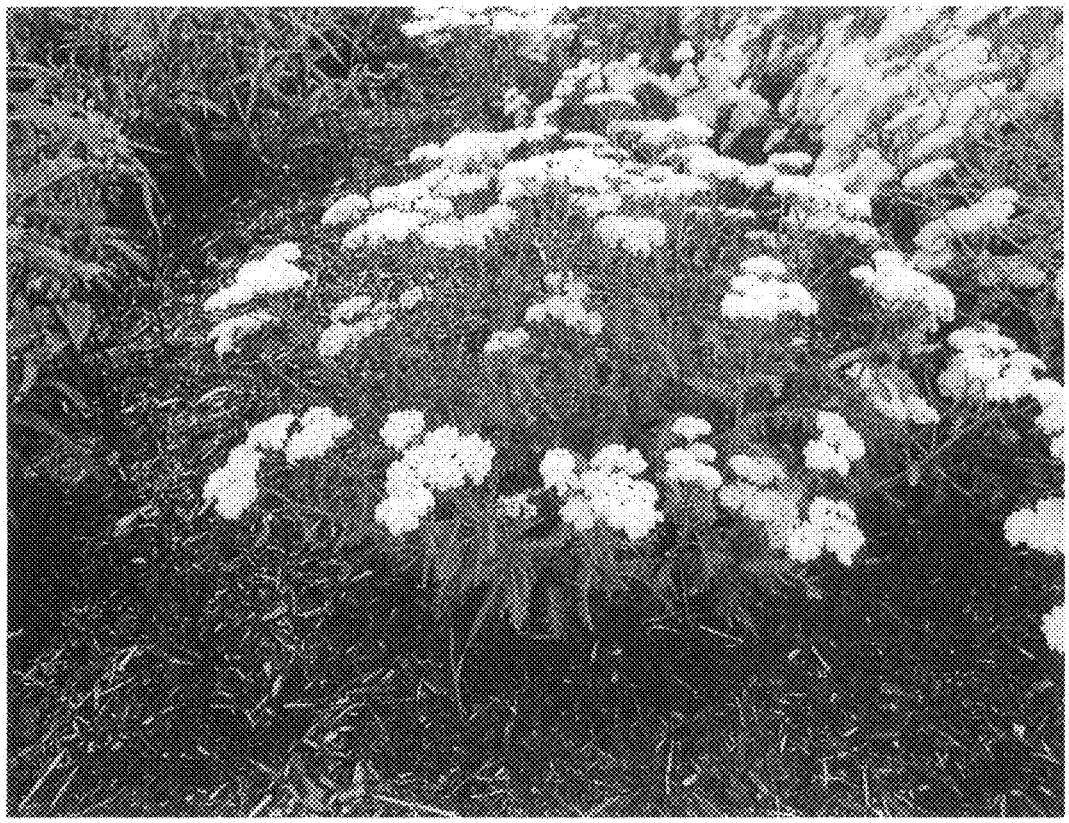

Botanical/commercial classification: *Achillea hybrida/ Achillea* Plant.

Varietal denomination: cv. Novaachdus.

SUMMARY OF THE INVENTION

*Achillea* plants commonly are recognized to be a member of the Asteraceae family and are sometimes identified by the Yallow or Milfoil common names.

The new *Achillea* plant of the present invention originated and was discovered at West Grove, Pa., U.S.A. during 2010. Seed was formed on the 'Moonshine' variety (non-patented in the United States) during 2008 as a result of open pollination. The male parent is unknown and may also be the 'Moonshine' variety. The seeds resulting from the pollination were sown in a controlled environment and the resulting plants were carefully observed and studied with respect to the exhibited phenotypic characteristics. Each of the resulting plants was observed to be physically and biologically different from the others. Selective study resulted in the identification of a single plant of the new variety.

It was found that the new *Achillea* plant of the present invention displays the following combination of characteristics:

(a) displays a considerably more compact and shorter growth habit than the 'Moonshine' variety (non-patented in the United States),
(b) displays attractive fine silvery-green mature foliage,
(c) is early-flowering with the formation of attractive soft light-yellow inflorescences that contrast nicely with the foliage coloration, and
(d) is well suited for providing ornamentation in parks and gardens.

The new plant of the present invention can be grown to advantage to provide distinctive ornamentation in the landscape.

The new plant can be readily distinguished from its maternal parent and all other *Achillea* varieties known to its discoverer, including the 'Sunny Seduction' variety (U.S. Plant Pat. No. 20,808). For instance, the 'Moonshine' variety, unlike the new variety, forms greener foliage, bright yellow blossoms, and displays a plant size that is up to approximately two times taller. The 'Sunny Seduction' variety also forms true green foliage, unlike the fine silvery-green foliage of the new variety. Additionally, the new variety commonly flowers a few days earlier than the 'Moonshine' variety and approximately nine days earlier on average than the 'Sunny Seduction' variety.

Asexual reproduction of the new plant at West Grove, Pa., U.S.A., through the rooting of cuttings has demonstrated that the distinctive characteristics are reliably transmitted from one generation to another. Accordingly, the new plant can be asexually reproduced in a true-to-type manner. When reproduced via the use of cuttings, a rooted cell commonly is formed in approximately 4½ weeks.

The new plant has been named 'Novaachdus', and will be marketed under the MOON DUST trademark.

BRIEF DESCRIPTION OF THE PHOTOGRAPHS

The accompanying photographs show as nearly true as it is reasonably possible to make the same in color illustrations of this character, typical specimens of the new variety. The illustrated plants had been asexually reproduced by the use of cuttings, were observed during June 2013 while approximately one year of age, and were being grown outdoors at West Grove, Pa., U.S.A.

FIG. 1 illustrates at the center a typical flowering plant of the new variety during the last week of June. The typical compact growth habit, soft light-yellow blossoms, and fine silvery-green foliage are shown. At the right and upper right the dissimilar bright yellow inflorescence of the 'Moonshine' variety is included for comparison.

Figure 2:
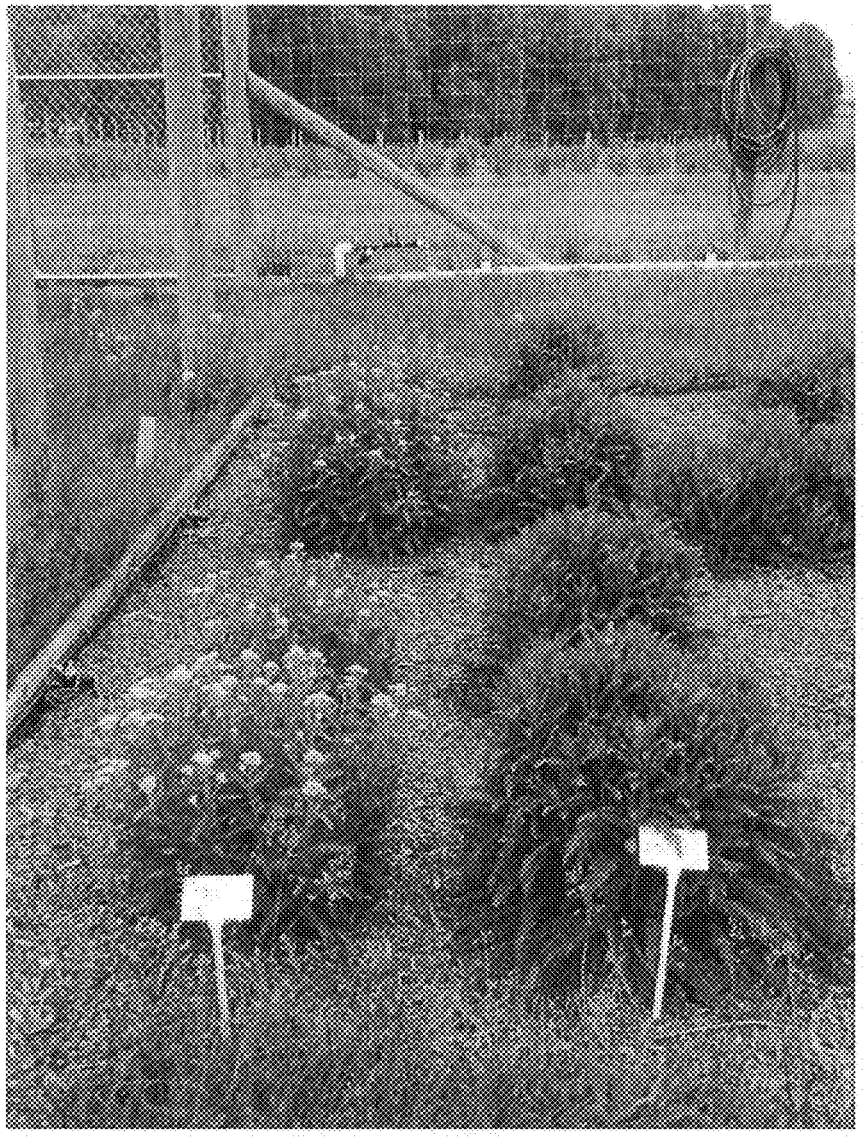

FIG. 2 further illustrates for comparative purposes in rows plants of the 'Sunny Seduction' variety on the right and the new variety of the present invention on the left. The photograph was taken during the first week of June. Unlike the 'Sunny Seduction' variety, plants of the new variety were well budded and had commenced blooming. A somewhat shorter growth habit also is displayed by the new variety. The 'Sunny Seduction' plants had just started to bud and were showing no flower color. Also, the mature foliage of the new variety is shown to be more silvery-green in coloration, unlike that of the previously known 'Sunny Seduction' variety.

DETAILED BOTANICAL DESCRIPTION

The following is a detailed description of the new plant of the present invention which was prepared while observing one-year-old plants growing outdoors during June 2013 at West Grove, Pa., U.S.A. Color terminology is in accordance with The R.H.S. Colour Chart (1995 or equivalent) of The Royal Horticultural Society, London, England, except when general color information is provided which is to be accorded customary dictionary significance.

Type: Herbaceous perennial for garden decoration and general landscape usage.

Parentage: Open pollinated seeding of the 'Moonshine' variety (non-patented in the United States).

Botanical classification: *Achillea hybrida.*

Plant:

*Growth habit.*—Compact and mounding.

*Height.*—Commonly approximately 12 to 14 inches on average. The new variety commonly assumes a mature height of approximately 30 cm on average, the 'Sunny Seduction' a mature height of approximately 38 cm on average, and the 'Moonshine' variety a mature height of approximately 60 cm on average.

*Width.*—Commonly approximately 12 to 14 inches on average. The new variety commonly assumes a mature width of approximately 30 cm on average, the 'Sunny Seduction' a mature width of approximately 21 cm on average, and the 'Moonshine' variety a mature width of approximately 30 cm on average.

*Branching.*—Commonly approximately 15 lateral branches on average per plant.

*Branch strength.*—Relatively strong.

*Branch length.*—Commonly approximately 24.5 cm on average.

*Branch diameter.*—Commonly approximately 3.5 mm on average.

*Internode length.*—Commonly approximately 2 cm on average.

*Aspect.*—Branches commonly disposed at approximately 30 degrees on average.

*Texture.*—Tomentose.

*Color.*—Greyed-Green Group 191A.

*Roots.*—As a fibrous network.

Foliage:

*Arrangement.*—Alternate, sessile.

*Shape.*—Lanceolate.

*Apex.*—Acute.

*Base.*—Truncate.

*Margin.*—Dissected, divided into many deep narrow segments.

*Length.*—Commonly approximately 16.3 cm on average for older leaves, and ranging to about 7 cm on average for newer leaves.

*Width.*—Commonly up to about 3 cm on average.

*Texture.*—Tomentose on upper and lower surfaces.

*Venation.*—Pinnipalmate.

*Color.*—Developing leaves: commonly are near Yellow-Green Group 144A on upper and lower surfaces. Fully expanded leaves: silvery-green on the upper surface near Greyed-Green Group 189A with venation near Green Group 138B, and on the lower surface near Green Group 137A with venation of Green Group 138B.

Inflorescence:

*Flowering.*—Throughout the season from May to late August, with flowering commonly beginning a few days earlier than the 'Moonshine' variety and approximately nine days earlier on average than the 'Sunny Seduction' variety at West Grove, Pa., U.S.A.

*Arrangement.*—Arranged in terminal or axillary compound cymes.

*Abundance.*—Commonly approximately 120 inflorescences develop per lateral branch.

*Bud shape.*—Ovoid.

*Bud length.*—Commonly approximately 6 mm on average.

*Bud diameter.*—Commonly approximately 2 mm on average.

*Bud texture.*—Tomentose.

*Bud color.*—Commonly near Yellow Group 4D in coloration.

*Cyme diameter.*—Commonly up to about 10 cm on average.

*Cyme height.*—Commonly approximately 6 mm on average.

*Inflorescence diameter.*—Commonly approximately 7 mm on average.

*Inflorescence depth.*—Commonly approximately 5 mm on average.

*Ray florets.*—Number: Commonly approximately six in a whorl. Shape: reniform. Length: commonly approximately 2 mm on average. Width: commonly approximately 3 mm on average. Apex: emarginate. Base: attenuate. Margin: entire. Texture: generally smooth on upper and lower surfaces. Color when opening: near Yellow Group 4B on the upper surface, and near Yellow Group 4D on the under surface. Color when fully open: near Yellow Group 11C on the upper surface, and near Yellow Group 4D on the under surface.

*Disc diameter.*—Commonly approximately 5 mm on average.

*Disc florets.*—Arrangement: clustered at the center. Shape: tubular with a five-pointed apex. Length: commonly approximately 4 mm on average. Diameter: commonly less than 1 mm. Number: commonly approximately 26 on average. Color when immature: commonly near Yellow Group 4D at the apex, near Yellow-Green Group 144B at the mid-section, and near Greyed-Green Group 193D at the base. Color when mature: commonly near Yellow Group 11D at the apex, near Yellow-Green Group 144A at the mid-section, and near Greyed-Yellow Group 193D at the base.

*Location of reproductive organs.*—With disc florets.

*Androecium.*—Stamen number: commonly approximately five on average. Filament length: commonly approximately 1 mm on average. Filament color: Yellow Group 11D. Anther shape: generally rounded. Anther size: less than 1 mm. Anther color: Yellow-Orange Group 15C. Pollen quantity: moderate. Pollen color: near Yellow-Orange Group 15A.

*Gynoecium.*—Pistil number one per floret. Pistil length: commonly approximately 3 mm. Stigma shape: biparted. Stigma color: Yellow Group 11D. Style length: commonly approximately 2 mm on average. Style color: near Yellow-Green Group 145D. Ovary color: near Green-White Group 157D.

*receptacle.*—Shape: generally ovoid. Diameter: approximately 4 mm on average. Height: approximately 4 mm on average. Color: commonly near Green Group 138D.

*Phyllaries.*—Number approximately 20 on average per inflorescence in four whorls. Shape: generally lanceolate. Length: commonly approximately 2 mm on average. Width: less than 1 mm. Apex: acute. Base: truncate and fused. Margin: entire. Texture: generally smooth on the upper surface, and pubescent on the under surface. Color: near Green Group 143C on the upper surface, and near Green Group 143A on the lower surface.

*Peduncles.*—Length: commonly approximately 8 mm on average for a terminal peduncle, approximately 1.4 cm for a fourth peduncle, and approximately 8 cm for a seventh peduncle. Diameter: approximately 1 mm on average. Strength: relatively strong. Aspect: generally upright and disposed approximately 40 degrees from the vertical. Texture: tomentose. Color: commonly near Greyed-Green Group 191A in coloration.

Development:

*Tolerance to diseases.*—During observations to date, the plant is believed to be typical of the genus.

*Resistance to pests.*—During observations to date, the plant is believed to be typical of the genus.

*Hardiness.*—Overwinters well at West Grove, Pa., U.S.A.

Plants of the 'Novaachdus' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Achillea* plant having the following combination of characteristics:

(a) displays a considerably more compact and shorter growth habit than the 'Moonshine' variety (non-patented in the United States), (b) displays attractive fine silvery-green mature foliage, (c) is early-flowering with the formation of attractive soft light-yellow inflorescences that contrast nicely with the foliage coloration, and (d) is well suited for providing ornamentation in parks and gardens;

substantially as illustrated and described.

* * * * *